United States Patent [19]

Hamilton et al.

[11] Patent Number: 4,767,747

[45] Date of Patent: Aug. 30, 1988

[54] METHOD FOR TREATING CONGESTIVE HEART FAILURE WITH N[6]-ACENAPHTHYL ADENOSINE

[75] Inventors: Harriet W. Hamilton, Chelsea; Robert P. Steffen, Saline, both of Mich.

[73] Assignee: Warner-Lambert Company, Morris Plains, N.J.

[21] Appl. No.: 901,107

[22] Filed: Aug. 28, 1986

[51] Int. Cl.[4] .................... A61K 31/70; C07H 19/16
[52] U.S. Cl. .................................. 514/46; 514/45; 536/24; 536/26
[58] Field of Search ...................... 514/46, 45

[56] References Cited

U.S. PATENT DOCUMENTS 4,614,732  9/1986  Hamilton et al. ................. 514/46
4,673,670  6/1987  Hamilton et al. ................. 514/46

FOREIGN PATENT DOCUMENTS 0179631  4/1986  European Pat. Off. ............ 514/46

*Primary Examiner*—Ronald W. Griffin
*Assistant Examiner*—L. Eric Crane
*Attorney, Agent, or Firm*—Elizabeth M. Anderson

[57] ABSTRACT

Method for treating congestive heart failure by administration of N[6]-[(1,2-dihydro-1-acenaphthylenyl)-methyl]adenosine or a pharmaceutically acceptable salt thereof.

3 Claims, 1 Drawing Sheet

METHOD FOR TREATING CONGESTIVE HEART FAILURE WITH N6-ACENAPHTHYL ADENOSINE

BACKGROUND ON THE INVENTION

The present invention is related to a method of using N6-[(1,2-dihydro-1-acenaphthylenyl)methyl]adenosine and certain pharmaceutically acceptable salts thereof as agents in treating congestive heart failure. The compound, a process for preparing it, and pharmaceutical compositions of the same are claimed in U.S. Pat. No. 4,614,732, which is herein incorporated by reference. The utility of the compound in the patent is for treating hypertension or coronary flow insufficiency.

SUMMARY AND DETAILED DESCRIPTION OF THE INVENTION

The present invention relates to a method of treating congestive heart failure in a patient in need of such treatment which comprises administering orally or parenterally in unit dosage form an effective amount of the prior known compound of the structural formula

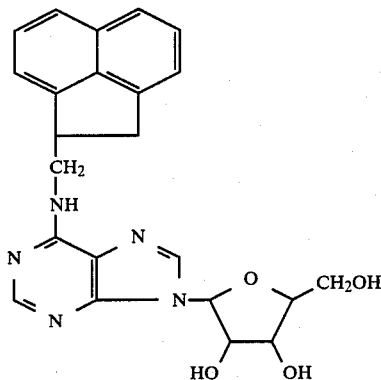

or a pharmaceutically acceptable salt thereof.

The compound of Formula I above is useful both in the free base form and in the form of acid addition salts and both forms are within the scope of the invention. Pharmaceutically acceptable salts within the scope of the invention are those derived from mineral acids such as hydrochloric and sulfamic, and organic acids such as ethanesulfonic, benzenesulfonic, p-toluenesulfonic, and the like, giving the hydrochloride, sulfamate, ethanesulfonate, benzenesulfonate, p-toluenesulfonate, and the like, respectively.

The acid addition salts of the basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compound used in the invention may contain asymmetric carbon atoms. The invention includes the use of its individual enantiomers or diastereomers which may be prepared or isolated by methods known in the art.

The usefulness of the compound and the salts thereof in the present invention as agents for congestive heart failure is demonstrated in standard pharmacological test procedures.

METHODS

Perfusion Technique

Figure 1:
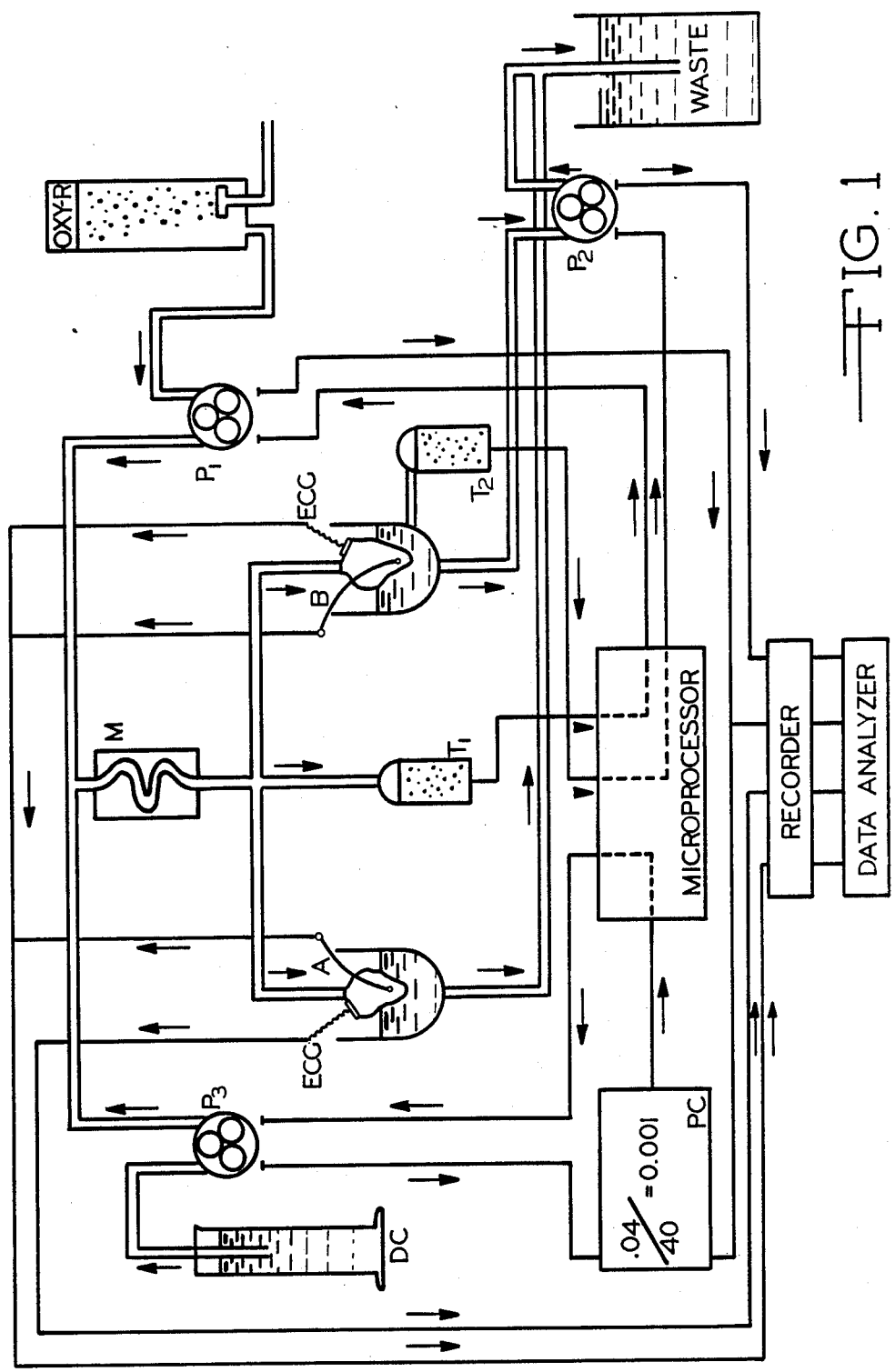
FIG. 1 depicts the microprocessor control system. $P_1$ is the coronary perfusion pump. $P_2$ is the coronary effluent pump. $P_3$ is the drug infusion pump. A and B are the two rat hearts. $T_1$ is the perfusion pressure transducer; $T_2$ is the heart chamber pressure transducer. DC is the drug concentration. M is the mixing valve. ECG is the electrocardiogram electrode. OXY is the oxygenator. PC is the proportioning circuit.

Male rats (400–600 gms) are pretreated with 2000 units Na heparin (Parke-Davis) and anesthetized with Na pentobarbital (50 mg/kg, Butler Co.) administered intraperitoneally. Once anesthetized, the rat heart is rapidly excised, the ascending aorta fitted to the aorta perfusion cannula, and secured with a ligature. The coronary arteries are perfused initially at a rate of about 15 ml/min for two to three minutes, after which they are perfused at constant pressure of 70 mm Hg and temperature of 37° C. The electrocardiogram (ECG) is recorded using two platinum electrodes positioned at the base and apex of the left ventricle (LV). The LV is instrumented via the mitral valve with a 4F Millar catheter tip pressure transducer. The catheter is advanced to the apex then withdrawn slightly. Once properly positioned, the catheter is anchored to the perfusion cannulae with an alligater clip. A second heart is excised, cannulated, and perfused by the same method outlined above. Both hearts are tested in parallel. The standard physiological salt solution is a modified Krebs Henseleit bicarbonate buffer of the following composition in mM concentration: NaCl, 127; NaHCO$_3$, 25; dextrose, 5.5; Na Pyruvate, 2.0; KCl, 4.7; MgSO$_4$, 1:1; KH 2PO$_4$, 1.2; CaCl$_2$.2H$_2$O, 2.5; CaNa$_2$ EDTA, 0.05.

A 30-minute stabilization period is observed before starting the test protocol.

Microprocessor Controlled Coronary Perfusion and Drug Delivery System

FIG. 1 depicts the microprocessor control system. This is a servo mechanism which permits coronary perfusion pressure (CPP) and drug concentration to be maintained constant independent of changes in coronary flow. The level at which CPP and drug concentration are maintained can be changed by commands communicated through the microprocessor keyboard. Dose-response curves are carried out by perfusing concentrated drug solution (DC) at rates proportional to total coronary flow (CF$_T$). Drug concentrations are increased by proportionate increases in the rate of DC infusion over CF$_T$ via the microprocessor keyboard. The proportional flow rates for DC:CF$_T$ is about 0.00005:1 at the low end and 0.0015:1 at the high end of the dose-response curve.

Dose-response curves encompassing at least two log doses are carried out in one-half log increments starting at a subthreshold dose and ending at a dose which produces near maximal response.

Measurements

Measurements for Cardiovascular Isolated Heart (CVIH) are maximum positive first derivative of LVP (LV+dP/dt$_{max}$), heart rate (HR), and coronary flow (CF). Units are: LV+dP/dt$_{max}$, millimeters of mercury/second (mm Hg/sec); HR, beats/minutes (bpm) and CF, milliliters/minute (ml/min). LV+dP/dt$_{max}$ is derived from the LVP signal by a differential amplifier and recorded. HR is calculated from the ECG strip chart recording and CF is calculated by recording analog outputs from pumps 1 and 2. Outputs from pump #1=$CF_T$ and the output from Pump #2=CF for heart B ($CF_B$). CF for heart A ($CF_A$) is calculated ($CF_T-CF_B=CF_A$). All pumps are calibrated weekly or when pump tubing is replaced.

Compound Quantity and Preparation

The typical quantity necessary to screen a compound (N=2) is about 20 mg. Compounds are solubilized in DMSO and diluted with water when possible.

Data Reduction and Report Format

Data is digitized and averaged with an in-lab microcomputer (Buxco) data analyzer.

The report format is screening data sheets. Percent change in HR, CF, and $LV+dP/dt_{max}$ are illustrated graphically and tabulated.

For example, in Table 1, below, the compound (Compound 1) is seen causing a significant and unexpected increase in left ventricular contractility in vitro using isolated rat hearts perfused by the Langendorff method. Left ventricular inotropic activity was measured from the first deviation of left intraventricular pressure (dp/dt), chronotropic activity from the electrocardiogram, and vascular activity from changes in coronary flow. The structurally similar adenosine analog, ($N^6$-[(R)-indan-1-yl]adenosine) (Compound 2) was evaluated in the same manner for comparative purposes. Results of the evaluation are summarized in Table 1 below.

pentobarbital (3.5 mg/kg/hr) via a cannula in the femoral vein. Systolic, diastolic, and mean arterial blood pressure were recorded continuously from the thoracic aorta via the right femoral artery using a Millar Instruments Micro-Tip catheter pressure transducer. Heart rate was derived from the arterial pressure wave form. Left intraventricular pressure and its first derivative (dP/dt) were recorded continuously using a Millar Instruments catheter pressure transducer advanced into the left intraventricular chamber from the left carotid artery. dP/dt was used as an index of left ventricular contractility.

A left lateral thoracotomy was performed at the fourth intercostal space, the pericardium incised, and the heart exposed. The circumflex coronary artery was dissected free of connective tissue and an electromagnetic flow probe positioned around the vessel proximal to the left common coronary artery. Circumflex coronary artery blood flow was measured continuously. A Gould thermodilution catheter was advanced to the pulmonary artery via the right jugular vein for the measurement of cardiac output. The left femoral vein was cannulated for drug infusion.

Following surgical preparation a thirty minute control period was allowed to assure stability and establish basal cardiovascular function. Upon completion of the control period a cardiac output measurement was made. Test animals received either Compound 1 and Compound 3. Treatment with test agents was started with each agent administered in rising stepped infusions of 30

TABLE 1

Effects of Compound 1 and 2 on Cardiodynamics in the Isolated Rat Heart

| Concentration Molar | % Change from Control | | | | | |
|---|---|---|---|---|---|---|
| | dp/dt | | Coronary Flow | | Heart Rate | |
| | Compound 1 | Compound 2 | Compound 1 | Compound 2 | Compound 1 | Compound 2 |
| $10^{-9}$ | 1 | | 8 | | −1 | |
| $3 \times 10^{-9}$ | 17 | | 50 | | 5 | |
| $10^{-8}$ | 35 | −3 | 75 | −1 | 5 | 1 |
| $3 \times 10^{-8}$ | 38 | −9 | 80 | 3 | −2 | −9 |
| $1 \times 10^{-7}$ | | −2 | | 28 | | −9 |
| $3 \times 10^{-7}$ | | −5 | | 36 | | −15 |
| $1 \times 10^{-6}$ | | −7 | | 42 | | −31 |
| $3 \times 10^{-6}$ | | 3 | | 46 | | −51 |

The present invention was evaluated in the anesthetized dog.

IN VIVO EVALUATION

Adult mongrel dogs (n=8) were anesthetized with sodium pentobarbital (32 mg/kg, iv). The trachea was intubated and the animals ventilated artificially with room air by a positive pressure respirator. Anesthesia was maintained by a continuous infusion of sodium minutes at each dose. At the end of each 30 minute period cardiac output measurements were repeated.

The reference compound was ($N^6$-[2,3-dihydrophenalin-2-yl)methyl]adenosine), an adenosine agonist of structural similarity, Compound 3. The results in Table 2 illustrate that Compound 1 of the present invention is unique in that, in addition to its potent coronary flow effects, it produces moderate inotropic and cardiac output increases.

TABLE 2

Cardiovascular Effects (% Change) of Compound 1 and Compound 3 in the Anesthetized Dog

| μg/kg/min | HR | | MBP | | DP/DT | | CBF | | CO | | TPR | |
|---|---|---|---|---|---|---|---|---|---|---|---|---|
| | Compound 1 | Compound 3 | Compound 1 | Compound 3 | Compound 1 | Compound 3 | Compound 1 | Compound 3 | Compound 1 | Compound 3 | Compound 1 | Compound 3 |
| 0.1 | 3.7 | — | 5.2 | — | 1.7 | — | 13.6 | — | −1.7 | — | 7.0 | — |
| 0.3 | 7.1 | 0.7 | 7.4 | −1.6 | 6.1 | 1.1 | 26.2 | 5.6 | 4.7 | 4.9 | 2.5 | −6.2 |
| 1.0 | −10.0 | −0.4 | 1.9 | 1.3 | 9.3 | 1.7 | 53.2 | 5.4 | 10.1 | 4.8 | −7.5 | −5.8 |
| 3.0 | −10.6 | −1.8 | −7.8 | −6.2 | 15.4 | −1.2 | 146.7 | 4.5 | 17.8 | 4.5 | −21.7 | −10.0 |
| 10.0 | — | −4.1 | — | −9.8 | — | −1.7 | — | 13.3 | — | 4.7 | — | −13.6 |
| 30.0 | — | −7.1 | — | −13.6 | — | −1.0 | — | 31.3 | — | 3.1 | — | −15.5 |
| 100.0 | — | −24.8 | — | 21.1 | — | −10.4 | — | 64.6 | — | −14.6 | — | −6.7 |

TABLE 2-continued

| | Cardiovascular Effects (% Change) of Compound 1 and Compound 3 in the Anesthetized Dog | | | | | | | | | | | |
|---|---|---|---|---|---|---|---|---|---|---|---|---|
| | HR | | MBP | | DP/DT | | CBF | | CO | | TPR | |
| μg/kg/min | Compound 1 | Compound 3 | Compound 1 | Compound 3 | Compound 1 | Compound 3 | Compound 1 | Compound 3 | Compound 1 | Compound 3 | Compound 1 | Compound 3 |
| 300.0 | — | −31.3 | — | −36.6 | — | −29.2 | — | 29.1 | — | −29.3 | — | −9.4 |

μg/kg/min
HR—Heart Rate, beats/min
MBP—Mean arterial blood pressure, mg Hg
dP/dt—1st derivative of left intraventricular pressure mm Hg/sec
CBF—Coronary blood flow, ml/min
CO—Cardiac output, l/min
TPR—Total peripheral resistance, mm Hg/l/min In summary, the unexpected in vitro and in vivo effects of the compound of the present invention on left ventricular contractility and cardiac output, which properties are lacking in compound of similar structure, provides for the utility of the compound in the treatment of congestive heart failure.

For the therapeutic use described above, the usual mammalian dosage range for a 70 kg human subject is from 5 to 500 mg per day or 0.07 mg to 7.1 mg per kg of weight per day; optionally in divided portions. Determination of the proper dosage for a particular situation is within the skill of the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil; sesame oil, olive oil, corn oil, and oil of theobroma; propylene glycol, glycerine; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primary liquid composition. The most satisfactory compositions are those in which a much higher proportion of the active ingredient is present.

Routes of administration of the subject compound or its salts are oral or parenteral. For example, a useful intravenous dose is between 0.001 and 1 mg/kg. A preferred intravenous dose is 0.01 to 1.0 mg/kg. A still further preferred dose is 0.03 mg/kg. A useful oral dose is 0.01 to 31 mg/kg. A preferred oral dose is 0.1 to 10 mg/kg. A still further preferred dose is 1.0 mg/kg.

Examples of formulations of the subject compound or its salts are:

EXAMPLE 1

Injectables $N^6$-[(1,2-dihydro-1-acenaphthen-1-yl)methyl]adenosine (Compound I) Water for injection USP q.s.

The hydrochloride salt of Compound I is dissolved in water and passed through a 0.2-micron filter. Aliquots of the filtered solution are added to ampoules or vials, sealed, and sterilized.

EXAMPLE 2

Syrups 200 mg Compound I/5 ml syrup

| | |
|---|---|
| Compound 1 | 12.5 g |
| Purified Water USP | 200 ml |
| Cherry Syrup qu | 1000 ml |

Compound 1 is dissolved in the water and to this solution the syrup is added with mild stirring.

EXAMPLE 3

Capsules 50 mg, 100 mg, or 200 mg

| | |
|---|---|
| Compound 1 | 250 g |
| Lactose USP, Anhydrous q.s. or | 250 g |
| Sterotex Powder HM | 5 g |

Combine Compound 1 and the lactose in a tumbel blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. The appropriately sized capsules are filled with 141 mg, 352.5 mg, or 705 mg fo the blend, respectively, for the 50 mg, 125 mg, and 250 mg containing capsules.

EXAMPLE 4

Tablets 50 mg, 100 mg, or 200 mg

| | |
|---|---|
| Compound 1 | 125 g |
| Corn Starch NF | 200 g |

-continued

| | |
|---|---|
| Cellulose, Microcrystalline | 46 g |
| Sterotex Powder HM | 4 g |
| Purified Water q.s. or | 300 ml |

Combine the corn starch, the cellulose, and Compound 1 together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 150 mg, 375 mg, and 750 mg, respectively, of the total mix are formed with appropriate sized punches the 50 mg, 125 mg, or 500 mg containing tablets.

We claim:

1. A method for treating congestive heart failure which comprises administering a therapeutically effective amount of a compound in unit dosage form having the structural formula

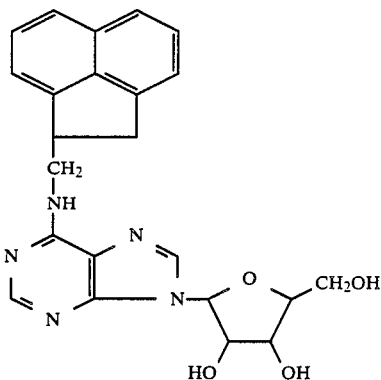

or a pharmaceutically acceptable salt thereof, to a mammal in need of said treatment.

2. The method of claim 1, wherein the compound is $N^6$-[(1,2-dihydro-1-acenaphthen-1-yl)methyl]adenosine.

3. The method of claim 1 wherein 0.0001 mg to 0.01 mg/kg of weight per day of the compound or the pharmaceutically acceptable salt is administered.

* * * * *